(12) United States Patent
Ohnishi

(10) Patent No.: US 6,538,023 B1
(45) Date of Patent: Mar. 25, 2003

(54) THERAPEUTIC USES OF GREEN TEA POLYPHENOLS FOR SICKLE CELL DISEASE

(76) Inventor: Tsuyoshi Ohnishi, 502 King of Prussia Rd., Radnor, PA (US) 19087

(*) Notice: Subject to any disclaimer, the term of this patent is extended or adjusted under 35 U.S.C. 154(b) by 0 days.

(21) Appl. No.: 09/663,455

(22) Filed: Sep. 15, 2000

(51) Int. Cl.[7] .............................................. A61K 31/35
(52) U.S. Cl. ....................................... 514/460; 514/456
(58) Field of Search .................................. 514/456, 460

(56) References Cited

U.S. PATENT DOCUMENTS 5,273,992 A * 12/1993 Brugnara et al. ............ 514/396

OTHER PUBLICATIONS

Grinberg L. N. et al., Abstract to "Protective effects of tea polyphenols against oxidative damage ot red blood cells", Biochem. Pharmacol. 54, No. 9, pp. 973–978, 1997.*

Zhang, A. et al., Abstract to "Inhibitory effects of jasmine green tea epicatechin isomers on free readical–induced lysis of red blood cells.", Life Sci. 61, No. 4, 383–394, 1997.*

Olivieri, O. et al., "Activation of K+/Cl–cotransport in human erythrocytes exposed to oxidative agents", Biochim Biophys Acta, Mar. 10, 1993, pp. 1176(1–2):34–42 [PubMed abstract].

Agil, A. et al., "Hydroxy–urea protects erythrocytes against oxidative damage", Redox Rep. 2000, 5(1), pp. 29–34 [PubMed abstract].

Iyamu, E.W., et al., "Hydroxyurea–induced oxidative damage of normal and sickle cell hemoglobins in vitro: amelioration by radical scavengers", J. Clin Lab Anal. 2000, 15(1):1–7 [PubMed abstract].

* cited by examiner

*Primary Examiner*—Dwayne C. Jones
(74) *Attorney, Agent, or Firm*—Caesar, Rivise, Bernstein, Cohen & Pokotilow, Ltd.

(57) ABSTRACT

The method of therapeutic management of sickle cell anemia involving oral administration to the patient of an effective dose of green tea polyphenols.

8 Claims, 4 Drawing Sheets

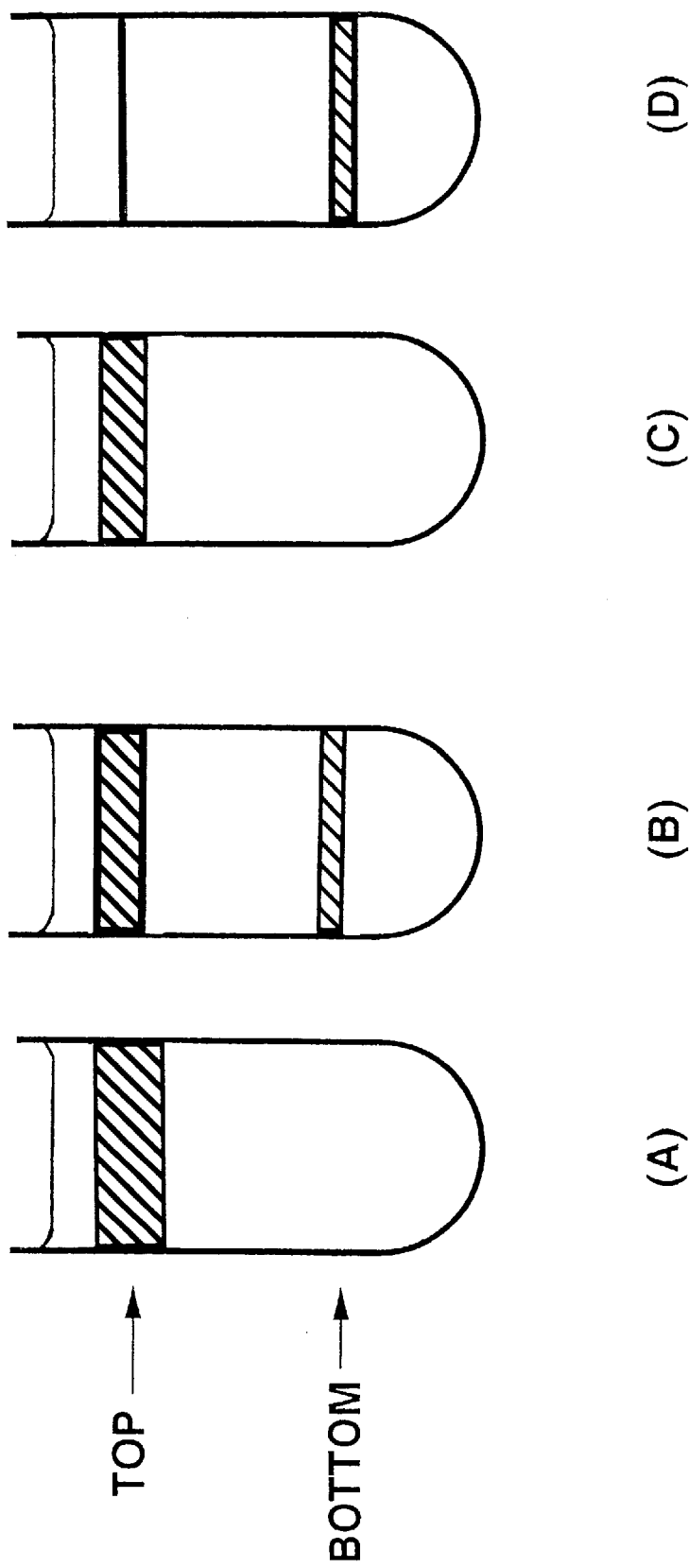
Fig. 2 (Amended)

THERAPEUTIC USES OF GREEN TEA POLYPHENOLS FOR SICKLE CELL DISEASE

BACKGROUND OF THE INVENTION

This invention relates to the therapeutic efficacy of green tea polyphenols for patients of sickle cell anemia (SCA). SCA is a serious disease generally found in a specific ethnic group, namely, African Americans and inhabitants of the African continent and nearby countries. In America, 1 out of every 500 of African descents suffers, but in Africa, the ratio is ten times higher. Approximate patient numbers are around 100,000 in the United States, but several millions in Africa. When sickle cell crisis occurs, the patients experience severe pain which is caused by the occlusion of blood vessels jammed with red blood cells. Since the average life span of their red blood cells is only about two weeks as opposed to about 120 days for normal subjects, the patients suffer from chronic anemia. Frequently observed symptoms are: acute chest syndromes, splenic infarction; cardiomegaly; neurological disorders such as hemiplegia, convulsions, coma and stupor; pathologic bone abnormalities such as marrow expansion, avascular necrosis, and osteomyelitis; and leg ulceration. In Africa, SCA causes high mortality in infants and children. Their survival rate to adulthood in Africa is less than 50%. Even though the patients' survival to adulthood is not uncommon in the United States, SCA is a disastrous disease.

Considering the demographics of SCA, the best hope for the majority of patients would be a low cost self-administered oral therapy. Currently, one such hope for these patients is oral administration of hydroxyurea. This is designed to increase the level of fetal hemoglobin which does not polymerize under deoxygenation. Hydroxyurea therapy has been shown to have beneficial effects, but it is still not free of side effects including bone marrow suppression. If the suppression develops, the patients have to stop the medication until the bone marrow could recover. Since SCA is a genetic disease, any drugs would have to be taken for life-long. There is no guarantee that the prolonged administration of hydroxyurea might cause undesirable side effects. Therefore, a safer method is urgently needed.

SUMMARY OF THE INVENTION

The inventor found from in vitro experiments that green tea polyphenols could inhibit dense cell formation by inhibiting K-Cl cotransport phenomenon across the sickle red blood cell membrane. This K-Cl cotransport is the major mechanism by which sickle cells are dehydrated in the circulation. It has been shown that the formation of dense cells is the triggering cause for sickle cell crisis (Ballas, S. K. and Smith, E. D. Blood 79:2154–2163, 1992; Fabrey, M. E., Benjamin, L., Lawrence, C. and Nagel, R. L. Blood 64:559–563, 1984).

Therefore, the prevention of dense cell formation would solve many of the problems from which the patients are suffering. Here, we propose a new therapy of SCA by oral administration of green tea polyphenols, such as Polyphenon™ E or its purified components, at the dosage of 200 mg to 1,000 mg/50 kg body weight of the patients/day. A preferred dosage is 600 mg/50 kg body weight of the patients/day. Green tea polyphenols are known to be safe. For example, the acute oral toxicity ($LD_{50}$) of Polyphenon™ E, in which Epigallocathechin gallate (EGCg) is the major component as shown in Table 1, is 1.5 gram/kg body weight in mice.

Many attendant features of this invention will become readily appreciated as the same becomes better understood by reference to the following detailed description when considered in connection with the accompanying drawings:

Examples of this invention are set forth below. However, it is to be understood that these examples are given by way of illustration only and are not to be construed as limiting the invention either in spirit or in scope, as many modifications both in doses and methods could be possible to those skilled in the art.

Experimental Design and Results

Methods

Green Tea Polyphenols Used in in vitro Studies

The structures of green tea polyphenols are shown in FIG. 1. Each compound was suspended in water, incubated in a boiling water bath for 10 seconds for complete solubilization, and used immediately.

Solutions

The reaction medium consists of: 150 mM NaCl, 1 mM $MgSO_4$, 10 mM HEPES buffer and 10 mM glucose. The osmolarity of the medium was adjusted to 290 mOsm/kg using a freezing point osmometer and the pH was adjusted to 7.4

A stock solution of percoll was prepared as follows. To a 100 ml Percoll solution (Pharmacia Biotech, Pistcataway, N.J.), 117 mM NaCl, 20 mM $KH_2PO_4$, 0.005 g each of penicillin and streptomycin were added. The pH was adjusted to 7.4. The osmotic pressure of this solution was adjusted to 290 mOsm/kg. The density as determined with a picnometer was 1.1365.

A stock solution of diatrizoic acid (Sigma Chemicals, St. Louis, Mo.) was prepared as follows: To 80 ml water, 115 mM diatrizoic acid was added. Then, 8 ml of 2M NaOH was added to solubilize the compound. Then, 20 mM $KH_2PO_4$, was added and the pH adjusted to 7.4 with 1 M HCl. Finally, the volume of the solution was made to 100 ml and the osmolarity was adjusted to 290 mOsm/kg. The density was 1.0475. A density gradient solution with the density of 1.104 was prepared by mixing one volume of the percoll stock solution and 0.422 volume of the diatrizoic acid stock solution.

Blood

For in vitro tests, blood was obtained from adult sickle cell patients (using acid-citrate-dextrose as an anticoagulant) whose hemoglobin F content is less than 1% and whose content of irreversibly sickled cells is less than 10%. The blood could be used for 2 days as long as the air-space of the container was equilibrated with 95% air/5% $CO_2$ and the container was gently tumbled (1 to 2 rpm) at 4° C.

Density Gradient Separation of Blood

Four ml of the density gradient solution (density=1.104) was poured into each of 15 ml COREX centrifuge tubes (Corning Glass), and the tubes were spun at 10,000 rpm for 5 min, by which a density gradient was automatically formed. Then, 100 μl of blood was overlayered on top of each pre-formed density gradient, and the tubes were span for 10 minutes at 2,500 rpm using a low speed centrifuge with a swing rotor.

When red blood cells of normal subject with normal hemoglobin were spun, they all stayed near a top portion of the gradient (FIG. 2A). When red blood cells of sickle cell patients were spun, they were separated into two layers as shown in FIG. 2B, namely, a light fraction with the density lighter than 1.104 (top layer) and a heavy dense cell fraction with the density higher than 1.104 (bottom layer). Then, the red blood cells in the top layer of each tubes, which consists of "non-dense cells", were collected, washed with the reaction medium, resuspended in the same medium, and used for the experiments.

Density Gradient Separation of Dense Cells Formed During the K-Cl Cotransport Experiments As described above, tubes each containing 4 ml of the density gradient solution with the density of 1.104 were spun at 12,000 rpm for 5 min to form gradient density. K-Cl cotransport experiments were conducted by incubating a suspension of "non-dense cells" with the hematocrit value of 2% at 37 centigrade for 3 hours. Then, 50 $\mu$l of each non-dense cell suspension was overlayered on top of the pre-formed density gradient, and the tubes were span for 10 minutes at 2,500 rpm using a low speed centrifuge with a swing rotor. When 500 mM urea was not added, no dense cells were formed as shown in FIG. 2C. If 500 mM urea was added before the incubation, dense cells were formed due to the stimulation of K-Cl cotransport as shown in FIG. 2D.

When the bottom layer was formed, red cells in both the top and bottom layers were separately collected, washed and hemolyzed in 5 mM phosphate buffer (pH 7.4) containing 0.5 mM EDTA and 0.5% of a detergent, BRIJ-30. From the hemoglobin content as determined by spectrophotometry, we determined the percentage of dense cell formation (Ohnishi, S. T. British J. Haematology 55:665–671, 1983).

Examples of Experimental Results

1. The following results demonstrated that dense cell formation caused by triggering K-Cl cotransport with 500 mM urea in in vitro experiments was inhibited by tea polyphenols.

As shown in FIG. 3, when a suspension of sickle red blood cells (non-dense cells prepared as described above) with the hematocrit value of 2% was incubated at 37 centigrade for 3 hours in the presence of 500 mM urea, about 90% of red cells became dense cells as indicated by "CONT." If urea was not added, no dense cells were formed as indicated by "NO UREA." When specific inhibitors for K-Cl cotransport, such as okadaic acid (OKA) and calyculin A (CALA), they inhibited the dense cell formation completely at a very small dose, namely, at 100 nM and 25 nM, respectively.

Vitamins C and E had no inhibitory effect, but EGCg, a major components in Polyphenon™ E, effectively inhibited dense cell formation at levels of 0.2–0.6 mM.

2. FIG. 4 show the results where several green tea polyphenols were tested. In this experiments, the non-dense cell suspension were incubated under either (1) oxygenated condition in ambient air, or (2) deoxygenated condition where tubes were purged with 100% nitrogen gas. The results show that K-Cl cotransport took place in both oxygenated and deoxygenated conditions. Different green tea compounds had different effects. CH and EC had no effects, but ECg, EGC and EGCg had a significant effect at 0.6 mM. In these three compounds, EGCg, a major component of Polyphenon™ E, had the maximum inhibitory effect.

The Significance of this Invention

K-Cl cotransport is the major cause of sickle red cell dehydration. Therefore, if we can inhibit this cotransport, we are expected to decrease the occurrence of sickle cell crisis, or even prevent sickle cell crisis. The reasons why this phenomenon are important are as follows:

(1) K-Cl cotransport can happen even in oxygented blood (Lauf P. K. et al. Am. J. Physiol.263:C917–932, 1992). It is well known that deoxygenation cause red cell sickling, which could subsequently trigger dehydration. However, this phenomenon can happen equally in the oxygenated blood.

(2) Urea can trigger K-Cl cotransport (Lauf P. K. et al. Am. J. Physiol.263:C917–932, 1992). In the kidney, blood are exposed to a high concentration of urea. This cotransport phenomenon is triggered in vitro even by 100 mM urea. Therefore, this could happen under normal physiological condition.

(3) A low pH can cause K-Cl cotransport (Brugnara C. et al. Blood. 70:1810–1815, 1987). It is well known that acidosis caused by increased physical activity often triggers sickle cell crisis. In in vitro experiments, this phenomenon even exists at physiological pH, namely 7.4, and it sharply increases below this pH, reaching the maximum at pH 6.8. Therefore, dehydration caused by K-Cl cotransport is expected to frequently happen in the SCA patients.

(4) We found that Vitamin C and vitamin E was ineffective in inhibiting K-Cl cotransport. It is well known that the serum antioxidant level of SCA patients is about a half of that in normal subjects with normal hemoglobin. Therefore, the patients are under heavy oxidative stress. However, the supplementation by vitamin C and vitamin E did neither improve physical conditions of SCA patients nor prevent crisis. This has been a puzzling question for-investigators who study SCA. Our results suggest that the lack of effects of these vitamins is related to their ineffectiveness to inhibit K-Cl cotransport which is the major mechanism of cell dehydration.

(5) Green tea polyphenols are strong antioxidants. Therefore, in addition to their effects in inhibiting K-Cl cotransport phenomenon, they could improve general health condition of the patients by increasing serum antioxidant levels.

TABLE 1

| Composition of catechins in Polyphenon ™ E. | |
|---|---|
| Catechins | Content (%) |
| (–)-Epicatechin (EC) | 9.39 |
| (–)-Epigalloactechin (EGC) | 5.55 |
| (–)-Epicatechin gallate (ECg) | 5.63 |
| (–)-Epigalloactechin gallate (EGCg) | 62.10 |
| Other catechins | 8.24 |
| Total | 90.91 |

BRIEF DESCRIPTION OF THE DRAWINGS

FIG. 2. Separation of red blood cells to non-dense cells (TOP layer) and dense cells (BOTTOM layer) by density gradient centrifugation.

(A) Red blood cells of a normal subject with normal hemoglobin do not have dense cells. (B) Red blood cells from a sickle cell patient contain a small percentage of dense cells. After density gradient centrifugation, the red cells in the top layer (non-dense cells) were collected, washed and used for the cell dehydration experiments. (C) When non-dense cells of the patients were incubated at 37 centigrade for 3 hours under oxygenated condition, no dense cells were formed. (D) When non-dense cells of the patients were incubated at 37 centigrade for 3 hours under oxygenated condition but in the presence of 500 mM urea, about 90% of red cells were dehydrated and formed dense cells.

Figure 1:
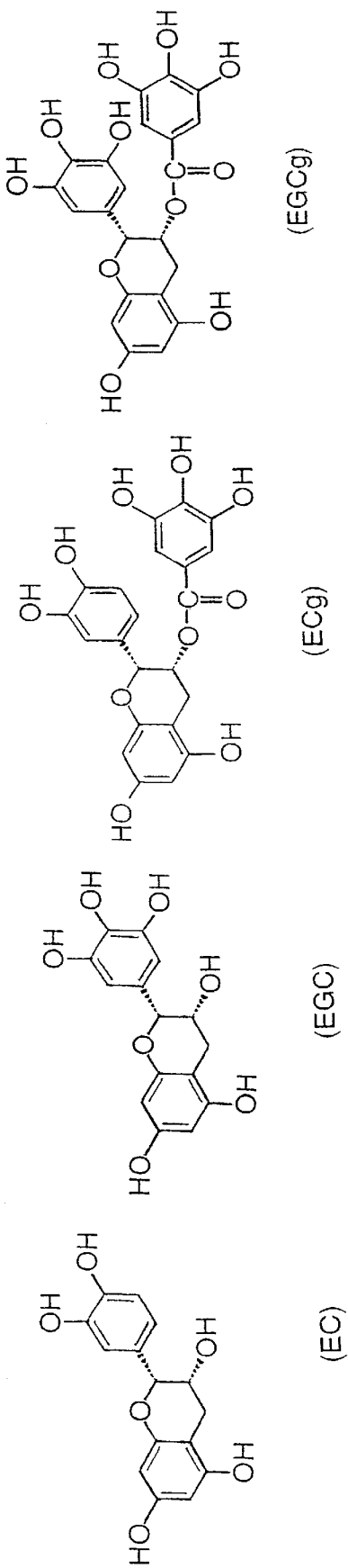
FIG. 1. The structures of tea polyphenols.
EC: epicatechin; EGC: Epigallocatechin; ECg: Epicathechin gallate; and EGCg:Epigallocathechin gallate.
Figure 3:
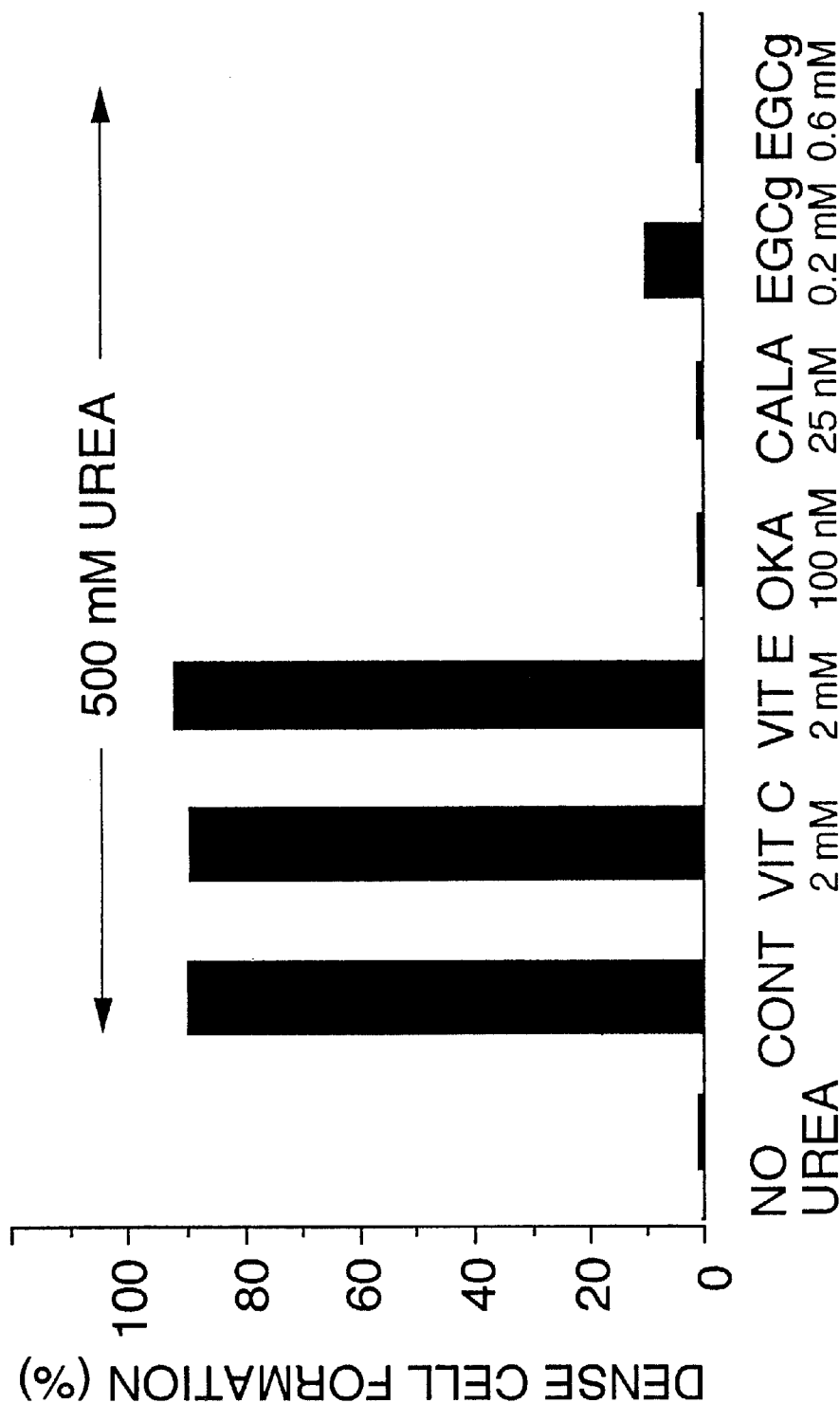

FIG. 3. Dense cells can be formed by incubating non-dense cells at 37 centigrade for 3 hours in the presence of 500 mM urea, which triggers K-Cl cotransport and concomitant dehydration. The ordinate shows the percentage of dense cell formation. The formation can be inhibited by the addition of inhibitors before starting the incubation. The figure shows that 100 nM of okadaic acid (OKA) or 25 nM of calyculin A (CALA), as well as 0.2 and 0.6 mM of a green tea polyphenol, EGCg, can inhibit dense cell formation. However, neither 2 mM vitamin C nor 2 mM vitamin E inhibited the dense cell formation.

Figure 4:
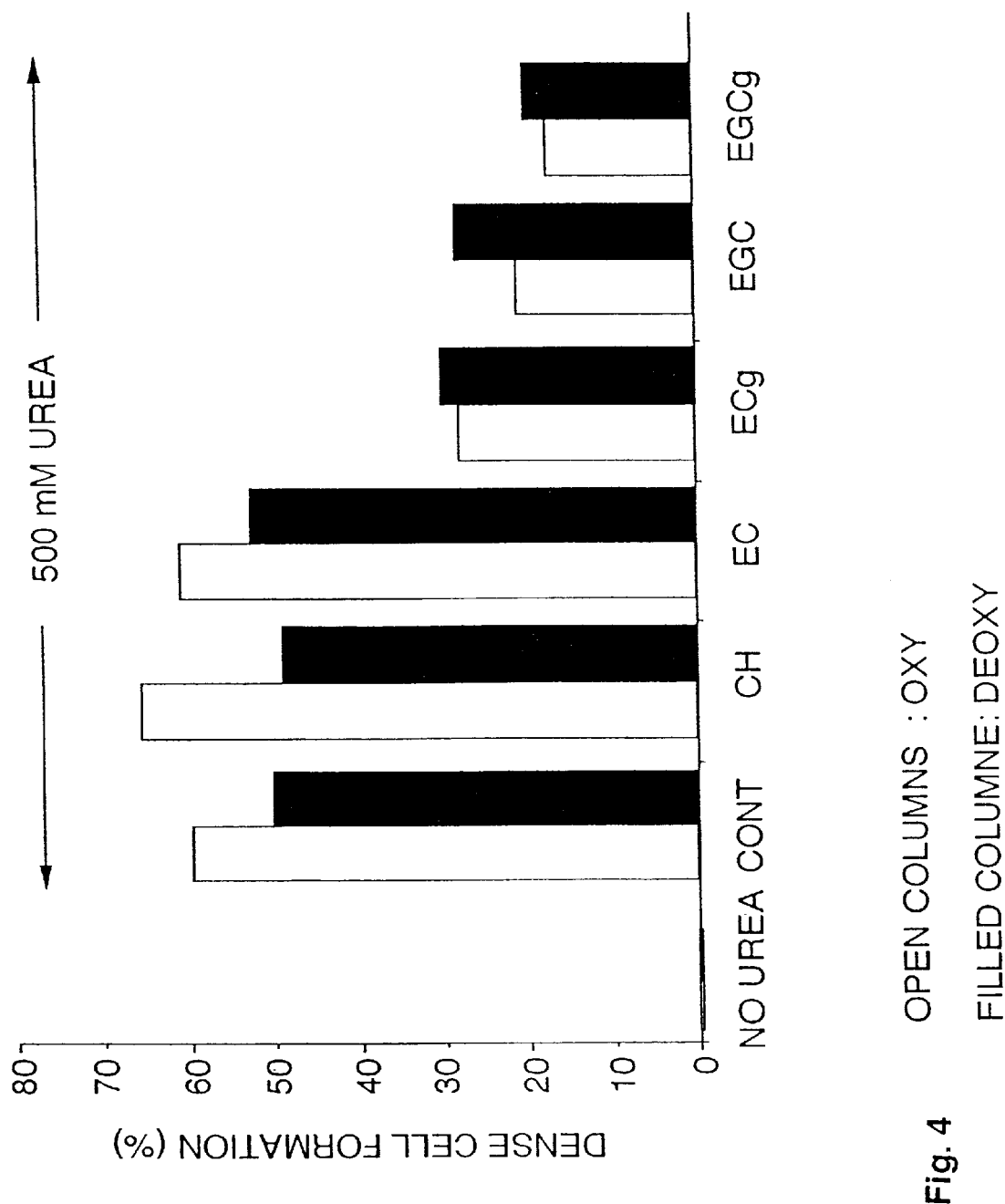

FIG. 4. The inhibition of dense cell formation triggered with 500 mM urea at 37 centigrade for 3 hours by different green tea polyphenols. Open columns are for the oxygenated condition and filled columns for the deoxygenated condition. Abbreviations. CH: (+)-Catechin; EC: (−)-Epicatechin; ECg: (−)-Epicatechin gallate; EGC: (−)-Epigallocatechin; and EGCg: (−)-Epigallocatechin gallate.

What is claimed is:

1. A method of inhibiting K-Cl cotransport in red blood cells of a patient with sickle cell anemia, said method comprising orally administering to the patient an effective dose of green tea polyphenols.

2. The method of claim 1, wherein said tea polyphenols include (−)-Epicatechin gallate; (−)-Epigallocatechin; and (−)-Epigallocatechin gallate.

3. The method of claim 2, wherein said green tea polyphenols are administered in a single dose per day.

4. The method of claim 2, wherein said administering procedure is performed multiple times per day with equal or unequal doses each time.

5. The method of claim 2, wherein said dose of green tea polyphenols is 200 mg to 1,000 mg/50 kg body weight of the patient/day.

6. The method of claim 2, wherein the said dose of green tea polyphenols is 600 mg/50 kg body weight of the patients/day.

7. The claim of 5, wherein said doses of green tea polyphenols are administered together with other therapeutic agents for sickle cell anemia.

8. The claim of 6, wherein the other therapeutic agents comprise of 15 to 30 mg hydroxyurea/kg body weight/day.

* * * * *